United States Patent [19]

Longenecker et al.

[11] 4,267,721
[45] May 19, 1981

[54] RESPIRATORY ANALYZER

[75] Inventors: Ned Longenecker, Lancaster; Clair M. Becker, Washington Boro; David P. Riegel, Landisville; Alan G. Vogt, Jr., Lancaster, all of Pa.

[73] Assignee: Timeter Instrument Corp., Lancaster, Pa.

[21] Appl. No.: 92,723

[22] Filed: Nov. 9, 1979

[51] Int. Cl.³ .............................................. G01L 27/00
[52] U.S. Cl. ....................................... 73/1 G; 73/168
[58] Field of Search ................. 73/1 R, 168, 432 SD, 73/1 G; 128/630

[56] References Cited

U.S. PATENT DOCUMENTS

| 3,054,288 | 9/1962 | Bowman et al. | 73/168 |
| 3,690,143 | 9/1972 | Day | 73/1 R |
| 4,109,505 | 8/1978 | Clark et al. | 73/1 R |

Primary Examiner—Jerry W. Myracle
Attorney, Agent, or Firm—Martin Fruitman

[57] ABSTRACT

An apparatus for testing and calibrating respiratory therapy equipment. A single compact unit is pre-programmed to automatically valve in each selected test, and display pertinent parameters in a digital format. The system includes two flow transducers, one each for high and low flows, a regulated heater to test thermometers, and measurement circuits for checking the electrical insulation integrity of the equipment tested.

9 Claims, 1 Drawing Figure

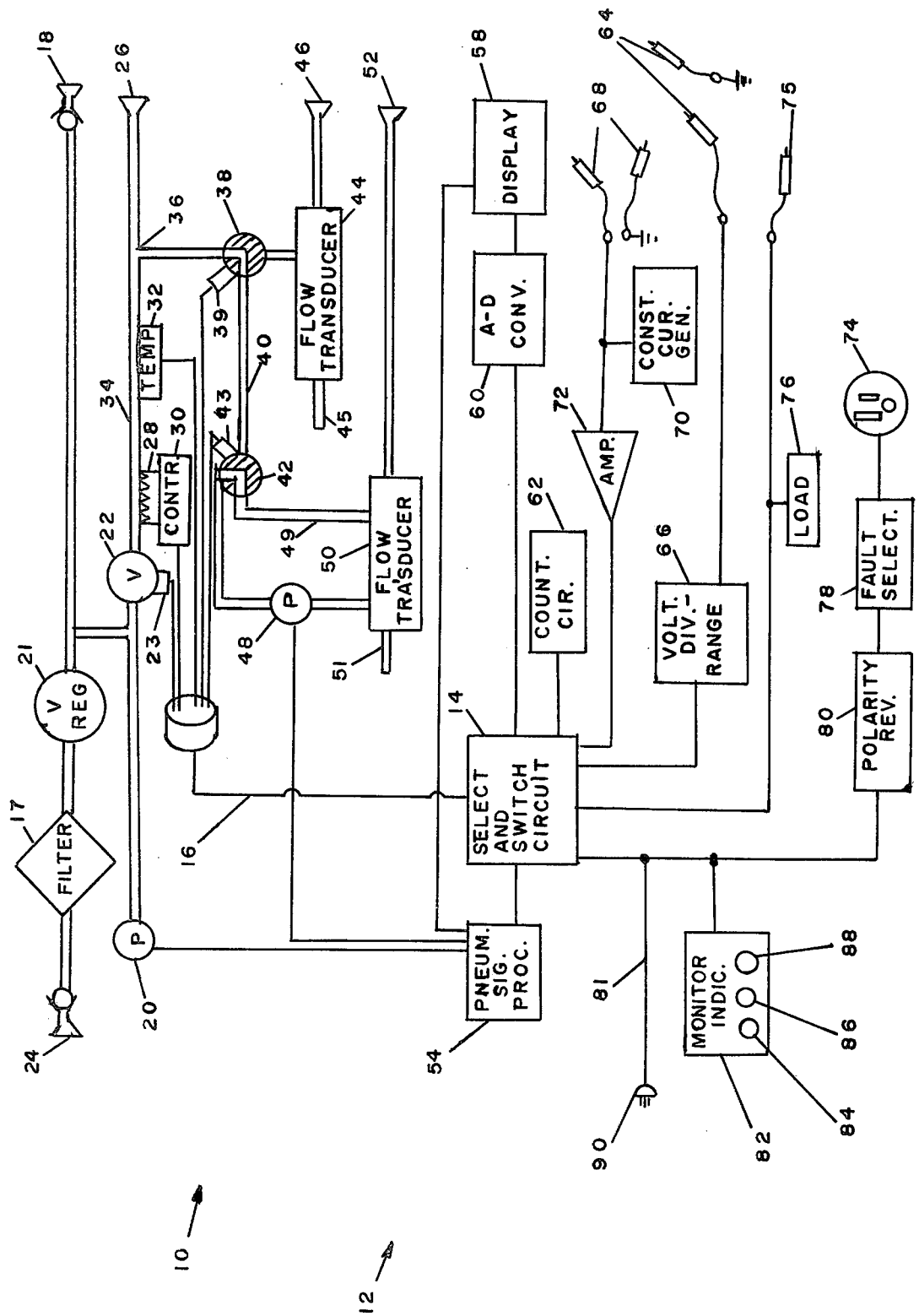

RESPIRATORY ANALYZER

BACKGROUND OF THE INVENTION

This invention deals generally with testing and calibrating equipment and more specifically with calibrating respiratory therapy equipment and checking it for electrical safety.

The sophistication of hospital care has increased immensely in recent years, and while most large hospitals have a considerable inventory of equipment to aid patients, the typical health care facility does not have either the staff or equipment to assure continued accuracy of that vital equipment.

When an industrial installation has as much equipment as a hospital respiratory therapy department, it has a regular program of calibration of all equipment and a considerable staff to carry it out. But despite a vital need for accuracy in the medical field, the methods of verifying the accuracy of life saving respiratory equipment have not kept pace with the equipment itself.

Virtually every parameter is presently tested by a separate piece of calibration equipment. Moreover, the calibration equipment is slow in operation, bulky, costly and complex. This is generally because the equipment presently in use is essentially designed similar to primary standards. Air volume is, for instance, checked by actually displacing a measurable volume enclosed within an expanding cylinder.

The essential need in the field of respiratory therapy is for a fast, accurate means of calibrating all the various parameters normally measured, with an apparatus which is simple enough and dependable enough for any operator to achieve reliable results with minimum training. Moreover, since a device with faulty wiring can cause serious injury or death to a patient, there exists an important need for a device to check the electrical safety criterion of all respiratory therapy equipment on a regular basis.

SUMMARY OF THE INVENTION

The present invention fulfills both the need for fast, accurate calibration and that of electrical safety checks, by combining all necessary calibration and testing systems in a single compact cabinet unit. The unit is pre-programmed so the user need only make interconnections between the present invention and the device to be tested, select the parameter desired to be tested and read the results in a simple, unambiguous digital format.

The unit requires an oxygen source and it includes a regulator, a heater, two flow transducers, two pressure transducers, a temperature transducer and three flow valves in its gas flow circuitry. However, the novel arrangement of these components, electrical switching, analog to digital conversion circuitry and electronic timing, permit the multiple use of these few elements to yield accurate calibrations for vital respiratory parameters.

The compact analyzer calibrates low pressures to 100 cm. of water; low vacuum to negative 100 cm. of water; line pressures to 70 psig; suction vacuum to negative 20 inches of mercury; filter back pressure up to 100 cm. of water; temperatures in both celsius (36°-38°) and Fahrenheit (98°-99°); oxygen flow rates in two ranges of ½ to 5 liters per minute and 7 to 70 liters per minute; tidal volume in the range of zero to two liters of oxygen; and breath rate in the range of 2 to 60 breaths per minute.

The analyzer also performs the following electrical tests: D.C. voltage; A.C. voltage; A.C. and D.C. current leakage from chassis to ground; resistance of the ground connector on power cords; and checks for proper polarity and ground integrity of all electrical outlets.

Each of these tests is accomplished without special hookup by the operator, since the electronic switching circuit, following the activation of the selected tests, makes all gas line and electrical hookups which are appropriate for each individual test.

BRIEF DESCRIPTION OF THE DRAWING

The FIGURE is a combined gas flow and electrical block diagram of the preferred embodiment of the invention.

DETAILED DESCRIPTION OF THE INVENTION CONFIGURATION OF THE PREFERRED EMBODIMENT

The preferred embodiment is pictured in schematic block diagram form in the FIGURE, where gas lines 10 and associated control devices are controlled by electronic circuitry 12 and all are enclosed within a single cabinet.

Selecting and switching circuit 14 acts as a master control so that as each test is selected by activating a specific switch (not shown), the appropriate electronic switching and valving is accomplished to perform the test and display the results on the digital display. A control unit such as the selecting and switching circuit is well within the capability of one skilled in electronic control art, and can be based upon either switch, relay, semiconductor or computer technology. Cables 16 supply control impulses to the valves and transmit various measurements to switching circuit 14 for processing and display.

High pressure outlet and vacuum inlet 18 is interconnected to pressure transducer 20, regulator 21, and control valve 22. Regulator 21 is supplied through filter 17 by inlet 24 which, in use, is connected to an oxygen source (not shown). Valve 22 controls the flow between temperature/filter resistance outlet and low pressure/vacuum inlet 26 and regulator 21. Adjacent to valve 22, controlled by solenoid 23, are located heater 28 and its controller 30 and temperature transducer 32. Heater 28 heats pipe 34 in order to raise the temperature of the gas flow within it, and temperature transducer 32 measures the temperature of the gas flow. "T" 36 taps the gas flow from pipe 34 and directs it to valve 38 where it can optionally be cut off or connected to pipe 40 and valve 42.

Valve 38, controlled by solenoid 39, can also connect pipe 40 to the input end of low flow transducer 44, which is also connected to low flow inlet 46. The downstream end 45 of flow transducer 44 is open to atmosphere.

Valve 42, controlled by solenoid 43, optionally interconnects pressure transducer 48 with either pipe 40 or pipe 49 and the upstream end of high flow transducer 50. The downstream end 51 of flow transducer 50 is open to atmosphere. The upstream end of flow transducer 50 is connected to high flow/tidal volume/breath rate inlet 52.

The electrical circuitry all converges upon selecting and switching circuit 14. The gas controls and transducers are connected to switching circuit 16 by multiple cables 16, shown as a single cable as it enters selecting and switching circuit 14. Also connected to selecting and switching circuit 14 is pneumatic signal processor 54 which generates digital signals and conditions analog signals from pressure transducers 48 and 20. Pneumatic signal processor 54 also generates timing functions required for counter 62 and display 58 in order to measure rate functions such as Tidal Volume and Breath Rate.

Selecting and switching circuit 14 channels all other measurement parameters to analog-to-digital converter 60 which displays the appropriate measurement on digital display 58.

Counting circuit 62 is interconnected through switching circuit 14 which accumulates and displays Breath Rate and Tidal Volume which are originally detected as an electrical signal from pressure transducer 48.

The electrical safety checks are also controlled by switching circuit 14. Voltage probes 64 are connected through voltage divider and range selector 66, and ground resistance test leads 68, connected to constant current generator 70, feed a signal to amplifier 72 which produces a voltage proportional to the ground resistance as indicated on digital display 58. Current leakage test lead 75 is connected to load 76 to generate a measurable voltage indicated on display 58, while switches 78 and 80 interchange power lines supplying test outlet 74 thereby simulating all possible fault conditions.

Line monitoring circuit 82 containing indicators 84, 86, and 88 is connected to input power cord 81 and plug 90. Indicators 84, 86, and 88, and the combination of their lights, indicate proper wiring of the power source for the Respiratory Analyzer, and also indicate the particular nature of many of the likely wiring faults.

OPERATION OF THE PREFERRED EMBODIMENT

For clarity of description, the operation of each test is described individually below:

Calibration of high pressure gauges or suction vacuum is accomplished by connecting the gauge to be tested to high pressure outlet and vacuum inlet 18 and activating a similarly named switch (not shown) within selecting and switching circuit 14. Valve 22 is then closed by solenoid 23 and switching circuit 14 connects pressure transducer 20 to analog-to-digital converter 60 for display of the pressure reading on digital display 58. Regulator 21 supplies oxygen at appropriate pressures for the high pressure test.

The calibration of low pressure or vacuum gauges is accomplished by connecting the device under test to low pressure inlet 26 and activating a similarly named test switch. Switching circuit 14 then closes valve 22 and, by use of solenoid 39, sets valve 38 to connect "T" 36 to pipe 40. Valve 42, by means of solenoid 43, connects pipe 40 to pressure transducer 48. The electrical output of pressure transducer 48 is conditioned by pneumatic signal processor 54 and A/D converter 60 with the equivalent pressure appearing on digital display 58.

Gas temperature gauges are calibrated by connection to outlet 26 and activating the gas temperature control. Valve 22 is opened permitting oxygen flow through pipe 34. The oxygen thus flows out through connector 26 to the device under test. Meanwhile, switching circuit 14 connects temperature transducer 32 to A/D converter 60 for display of the temperature and also activates heater controller 30 to operate heater 28. Heater controller 30 automatically maintains the temperature at a preselected temperature between 36° C.-38° C. or 98° F.-99° F.

Filter resistance is checked by connecting a filter to be tested to outlet 26 and activating a similarly labeled switch, thus opening valve 22 to furnish a flow of oxygen to the filter. Pressure transducer 48 is also connected to outlet 26 through valve 42, pipe 40, valve 38 and "T" 36. The back pressure of the filter under test is sensed by pressure transducer 48, then conditioned by pneumatic signal processor 54 and displayed on digital display 58.

High flow rates are checked by connecting the outlet of the device under test to inlet 52 and selecting that test. If an oxygen flow source is required, the upstream end of the device under test is connected to valved outlet 18. Gas flowing from the device under test flows through inlet 52, through flow transducer 50, and exits into the room, via pipe 51. Pressure transducer 48 is connected across flow transducer 50. Switching circuit 14 pulses solenoid 43 and valve 42 connects pressure transducer 48 to pipe 49. The output of pressure transducer 48 is conditioned by pneumatic signal processor 54 and A/C converter 60. The equivalent flow rate is directed by switching circuit 14 to digital display 58.

Low flow rates are checked by connecting the device under test to inlet 46 and, if needed, to outlet 18. Gas then flows through the device tested into inlet 46, through flow transducer 44 and pipe 45 into the room. Flow transducer 44 is connected to pipe 40 by valve 38. Pressure transducer 48 connects to pipe 40 through valve 42. The electrical output of pressure transducer 48 is conditioned by pneumatic signal processor 54 and channeled by switching circuit 14 to A/D converter 60 and displayed on digital display 58.

Tidal Volume is measured by connecting the device under test to inlet 52 and selecting the Tidal Volume test. The flow path is then through flow transducer 50. Pressure transducer 48 is connected to flow transducer 50 through valve 42. Switching circuit 14 connects the electrical output of pressure transducer 48 to counting circuit 62. The measured flow rate is integrated during each individual tidal cycle thereby providing an accurate display of gas volume.

Breath rate is tested by connecting the device under test to connector 52 and flow transducer 50. Flow transducer 50 connects to pressure transducer 48 by way of pipe 49 and valve 42. The electrical output of pressure transducer 48 is then interconnected with pneumatic signal processor 54 which creates a pulse as each pressure wave is sensed. Counting circuit 62 measures the pulse rate which is shown on display 58.

Ground resistance, the resistance of the ground wire in the power cord, is checked by connecting test leads 68 to the ground prong of a power cord and the chassis ground of the unit being tested. Selecting the test activates constant current generator 70 which creates a voltage across the ground wire. This voltage is sensed by amplifier 72 whose output is fed to A/D converter 60 and the equivalent resistance is shown on display 58.

Electrical current leakage to the chassis of a medical instrument is checked by plugging the device into test outlet 74, connecting leakage current lead 75 to the exposed metal surfaces of the device under test, and selecting the desired test at switching circuit 14. Load resistor 76 is used to produce a voltage equivalent to the leakage, measured and shown on display 58. Fault selector switch 78 is used to disconnect ground, and neutral wires on test outlet 74. Polarity reversal switch 80 interchanges hot and neutral wires supplying test outlet 74. The leakage current of the device under test is monitored and displayed by 58 during the fault simulation process.

AC and DC voltages can be monitored using the voltage probes 64 and selecting the appropriate range on switching circuit 14, which controls voltage divider and range selector 66. The measured voltage is switched to A/D converter 60 and shown on display 58.

Additional safety information is provided by testing the primary power source used by the Respiratory Analyzer. This is accomplished by connecting the power line 81, fed from hospital grade plug 90 into a hospital grade outlet. Monitoring indicator circuit 82 shows, by the particular combination of its three indicators 84, 86, and 88 whether the hot wire, ground wire and neutral wire are properly connected in the hospital grade wall outlet.

It is to be understood that the form of this invention as shown is merely a preferred embodiment. Various changes may be made in the function and arrangement of parts; equivalent means may be substituted for those illustrated and described; and certain features may be used independently from others without departing from the spirit and scope of the invention as defined in the following claims.

What is claimed as new and desired to be secured by Letters Patent of the United States is:

1. An apparatus for multiple function calibration and testing of respiratory therapy equipment comprising:
   a structural means;
   an electronically operated digital display located on a surface of the structural means;
   an analog to digital converter, the output of which is connected to the digital display;
   a selecting and switching means which activates pre-selected valves and connects pre-selected transducers to the analog to digital converter upon operation of any of several switches, each switch controlling a particular calibration procedure;
   a pneumatic signal processer, electrically connected to the selecting and switching means and to the digital display, capable of converting pressure information to electrical signals;
   a high flow inlet mounted upon the structural means;
   a high flow linear transducer the flow inlet side of which is connected to the high flow inlet;
   a high flow outlet connected to the flow outlet side of high flow transducer;
   a low pressure transducer the negative pressure side of which is connected to the low pressure output of the high flow transducer and the electrical output of which is connected to the pneumatic signal processor;
   a first selector valve, connected to and controlled by the selecting and switching means, the outlet of which is connected to the positive pressure inlet of the low pressure transducer, a first inlet of which is connected to the high pressure outlet of the high flow transducer and a second inlet of which is connected to the outlet of a second selector valve;
   a low flow inlet mounted upon the structural means;
   a low flow transducer, the flow inlet side of which is connected to the low flow inlet;
   a low flow outlet connected to the flow outlet side of the low flow transducer; and
   a second selector valve, connected to and controlled by the selecting and switching means, the outlet of which is connected to the second input of the first selector valve, a first inlet of which is connected to the high pressure output of the low flow transducer.

2. An apparatus for multiple function calibration and testing of respiratory therapy equipment as in claim 1, further comprising:
   a high pressure outlet mounted upon the structural means;
   a high pressure transducer, the electrical output of which is connected to the pneumatic signal processer, which is connected to the high pressure outlet;
   a high pressure gas regulator, the regulated side of which is connected to the high pressure transducer and the high pressure outlet;
   a high pressure inlet connected to the unregulated side of the high pressure gas regulator;
   a control valve, the inlet side of which is connected to the high pressure outlet, the high pressure transducer and the outlet side of the high pressure gas regulator, and the outlet side of which is connected to a second inlet of the second selector valve; and
   a low pressure inlet mounted upon the structural means and connected to the outlet of the control valve and the second inlet of the second selector valve.

3. An apparatus for multiple function calibration and testing of respiratory therapy equipment as in claim 2 further comprising:
   a thermal heating means electrically connected to and controlled by the selecting and switching means and heating a conduit connected to the outlet side of the control valve; and
   a temperature transducer, attached to the heated conduit at a location downstream from the heater, and electrically connected to the selecting and switching means.

4. An apparatus for multiple function calibration and testing of respiratory therapy equipment as in claim 1, further comprising:
   a power line monitoring circuit, connected to the power input lines of the circuit, containing three indicators the particular combination of lighted indicators indicating the connections of the power wiring.

5. An apparatus for multiple function calibration and testing of respiratory therapy equipment as in claim 1, further comprising:
   a counting means, connected to the pneumatic signal processer and the selecting and switching means, which measures the pulse rate of pressure changes sensed by the low pressure transducer and processed by the pneumatic signal processor.

6. An apparatus for multiple function calibration and testing of respiratory therapy equipment as in claim 1, further comprising:
   means to measure the resistance between the ground wire and chassis of an instrument under test.

7. An apparatus for multiple function calibration and testing of respiratory therapy equipment as in claim 1, further comprising:
   means to electrically isolate the instrument under test from ground and measure the leakage current to ground.

8. An apparatus for multiple function calibration and testing of respiratory therapy equipment as in claim 7, further comprising:
   means to reverse polarity and disconnect ground and neutral while measuring leakage current.

9. An apparatus for multiple function calibration and testing of respiratory therapy equipment as in claim 1, further comprising:
   voltage measuring means for external voltages.

* * * * *